US008702588B2

(12) United States Patent
Trzecieski

(10) Patent No.: US 8,702,588 B2
(45) Date of Patent: Apr. 22, 2014

(54) PLAY FLOW CONTROL APPARATUS AND METHOD FOR CONTROLLING A PLAY FLOW OF A SENSUAL CONSUMER PRODUCT

(76) Inventor: Michael Trzecieski, Hong Kong (HK)

(*) Notice: Subject to any disclaimer, the term of this patent is extended or adjusted under 35 U.S.C. 154(b) by 1125 days.

(21) Appl. No.: 12/431,064

(22) Filed: Apr. 28, 2009

(65) Prior Publication Data

US 2009/0270674 A1 Oct. 29, 2009

Related U.S. Application Data

(60) Provisional application No. 61/048,231, filed on Apr. 28, 2008.

(51) Int. Cl.
*A61F 5/00* (2006.01)

(52) U.S. Cl.
USPC .......... 600/38

(58) Field of Classification Search
CPC ....... A61H 19/00; A61H 19/50; A61H 19/34; A61H 19/44; A61H 23/0263; A61H 2201/50; A61H 2201/1685; A61H 2201/5038
USPC .......... 600/38–41
See application file for complete search history.

(56) References Cited

U.S. PATENT DOCUMENTS

| | | | | |
|---|---|---|---|---|
| 5,695,451 | A * | 12/1997 | Kawakami | 601/84 |
| 6,632,185 | B2 * | 10/2003 | Chen | 601/101 |
| 6,700,567 | B1 * | 3/2004 | Jaeger et al. | 345/179 |
| 7,438,681 | B2 * | 10/2008 | Kobashikawa et al. | 600/38 |
| 7,803,126 | B2 * | 9/2010 | Nan | 601/72 |
| 7,887,530 | B2 * | 2/2011 | Zemlok et al. | 606/1 |
| 2008/0207990 | A1 * | 8/2008 | Nan | 600/38 |

* cited by examiner

*Primary Examiner* — Samuel Gilbert
(74) *Attorney, Agent, or Firm* — Matthew A. Pequignot; Pequignot + Myers LLC

(57) ABSTRACT

A novel sensual consumer product is disclosed, this sensual consumer product utilizes a play flow control apparatus for receiving a user input for varying the play flow control signal for at least one of varying a mode of operation of a control circuit and the rotational speed of an electric motor. Rotating of the electric motor spins a weight and causes the sensual consumer product to vibrate. These vibrations are related to how the user mechanically interacts with play flow control apparatus, through touching or deforming of the sensual consumer product.

12 Claims, 3 Drawing Sheets

FIG. 3a
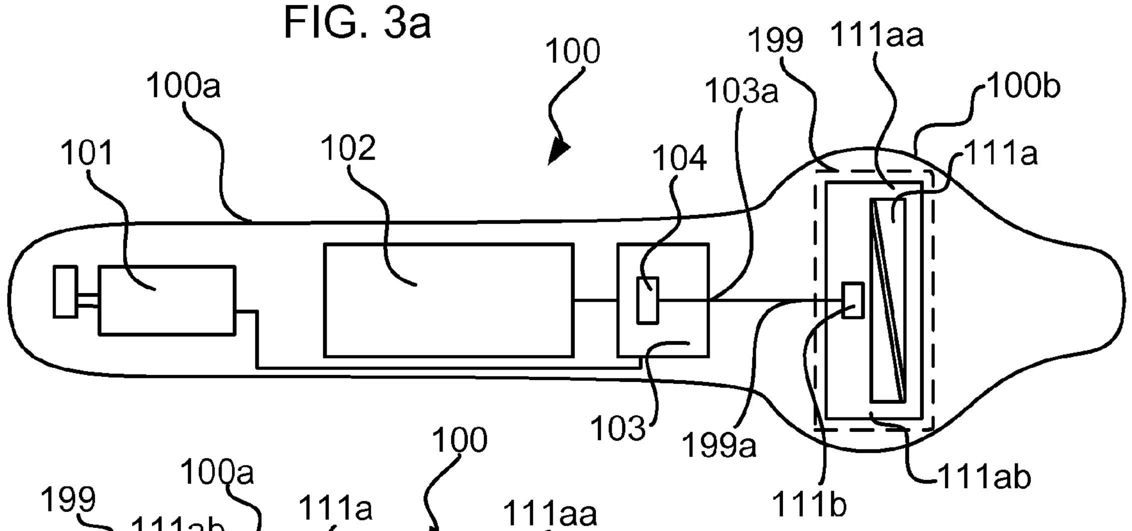
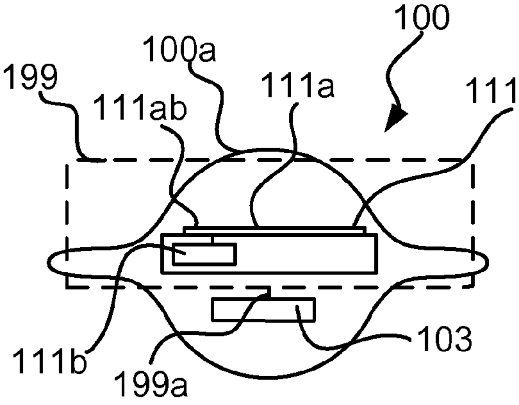
FIG. 3b
FIG. 4a
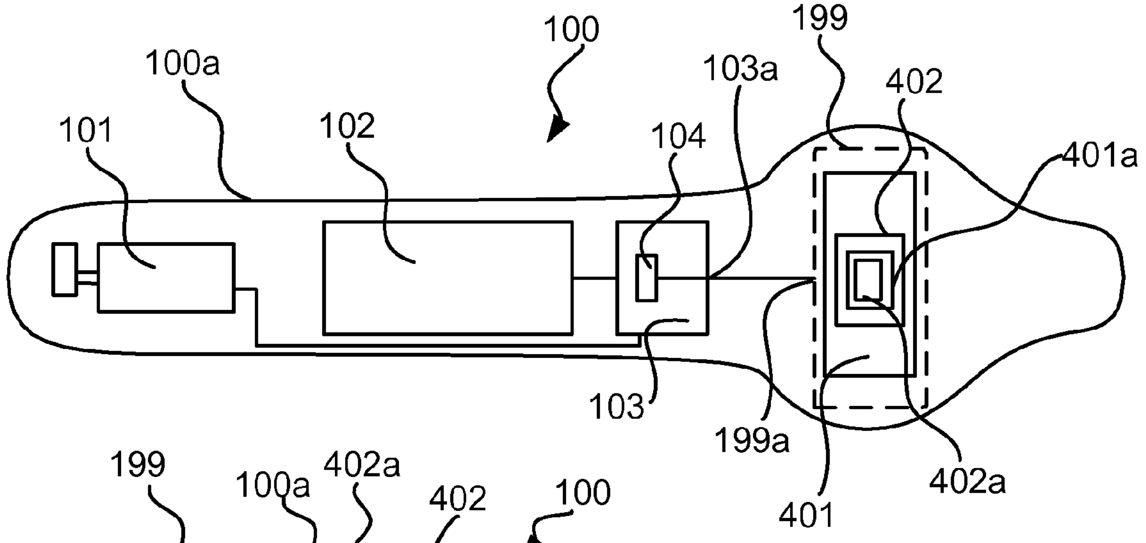
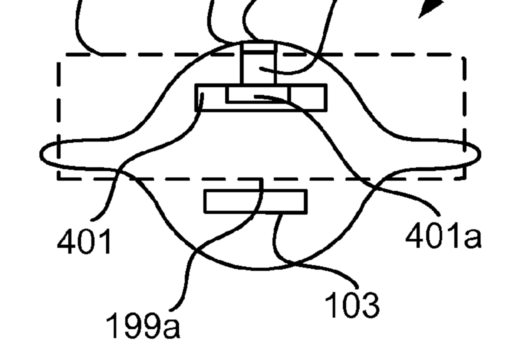
FIG. 4b

PLAY FLOW CONTROL APPARATUS AND METHOD FOR CONTROLLING A PLAY FLOW OF A SENSUAL CONSUMER PRODUCT

CROSS REFERENCE TO RELATED APPLICATION

This application claims priority from U.S. Provisional Application No. 61/048,231 filed on Apr. 28, 2008, the disclosure of which is incorporated herein by reference.

BACKGROUND

1. Field of the Invention

The field of invention relates generally to sensual consumer products and more specifically a play flow control apparatus and control method for varying a play flow of a sensual consumer product.

2. Background Information

Sensual consumer products are becoming more and more accepted by society. These sensual consumer products generally fall into two categories, those that are penetrator type devices and those that are layon type devices. Penetrator devices are made for penetrating inside of the body, whereas layon devices are used for external stimulation.

Traditional sensual consumer products are typically controlled using push button type switches and are typically not very advanced when it comes to the control system and apparatus that are used for varying their play flow, where the play flow is a changing in a rotation speed (RPM) of a motor or motors that are embedded within the sensual consumer product. As such their usage feels unnatural and unintuitive.

Transducers are electrical devices that convert one type of physical attribute to another, for example by converting a mechanical force into an electrical resistance. Capacitance sensors are electrical devices that detect capacitance of an object and provide an electrical signal in response thereto and are well known in the Art. An example of such a capacitance sensor assembly is found on state of the art MP3 players, such as the IPOD™ and those manufactured by Creative™. Typically a capacitance sensor assembly comprises a specially designed PCB (printed circuit board) as well as a capacitance sensing integrated circuit, where the two are electrically coupled in such a manner that when a user moves a body part, such as a finger, in proximity of the specially designed PCB, the capacitance sensing integrated circuit provides output signals that are representative of the movement of the body part past the specially designed PCB. An example of a capacitance sensing integrated circuit are those that are manufactured by Quantum™, www.Qprox.com Optical mice have become much cheaper in price over the past years and provide relative displacement and velocity information when the optical mouse is moved from a first position to a second position for two axes that are at an angle to each other. Typically these rates are up to 100 mm per second. The optical mouse assemblies have an optical path that requires an approximately fixed distance between an optical mouse sensor portion and an object that it brought into focus of the optical mouse sensor. Movement of objects past the optical path of the optical mouse imaging assembly results in signal to be generated by the optical mouse imaging assembly in dependence upon movement of an object past the optical path. Of course, the object must be at a proper distance from an optical sensor therein for the imaging to work properly, as is known to those of skill in the art.

It is therefore an object of the invention to provide a control system and apparatus for a sensual consumer product that overcomes the deficiencies of the prior art.

SUMMARY OF THE INVENTION

In accordance with the invention there is provided a sensual consumer product comprising: an electric motor having a rotational speed; a battery compartment; a housing having disposed therein the electric motor and the battery compartment, wherein the housing comprises at least a deformable portion; a play flow control apparatus disposed for receiving a user input and comprising an output port for providing a play flow control signal; a control circuit comprising a processor coupled with the electric motor and battery compartment and comprising an input port coupled with the output port of the play flow control apparatus for receiving of the play flow control signal therefrom, wherein, in use, a user input is provided to the play flow control apparatus for varying the play flow control signal for at least one of varying a mode of operation of the control circuit and the rotational speed of the electric motor.

In accordance with the invention there is provided a method comprising: providing a housing; providing a processor comprising instructions for being executed therein; providing an electric motor having an rotational speed and disposed within the housing; providing a play flow control apparatus; providing a control circuit coupled, having at least a mode of operation and comprising the processor, which is coupled with the play flow control apparatus and the electric motor; interacting with the play flow control apparatus; varying at least one of the rotational speed of the motor and the at least a mode of operation of the control signal in response to the interaction.

In accordance with the invention there is provided a sensual consumer product comprising: an electric motor; a battery compartment; a housing having disposed therein the electric motor and the battery compartment; a play flow control apparatus comprising at least one of: at least a transducer and an optical mouse imaging assembly and a capacitance sensing assembly, the play flow control apparatus disposed for receiving a user input and comprising an output port for providing a play flow control signal; a control circuit comprising at least a mode of operation and comprising a processor, where the control circuit is coupled with the electric motor and the battery compartment and comprising an input port coupled with the output port of the play flow control apparatus for receiving of the play flow control signal therefrom, wherein, in use, a user input is provided to the play flow control apparatus for varying the play flow control signal for at least one of varying the mode of operation of the control circuit and a rotational speed of the electric motor.

BRIEF DESCRIPTION OF THE DRAWINGS

FIG. 3*a* illustrates a top view and FIG. 3*b* illustrates an end view of a sensual consumer product (SCP) when the play flow control apparatus comprises a capacitance sensor assembly;

FIG. 4*a* illustrates a top view and FIG. 4*b* illustrates an end view of a sensual consumer product (SCP) when the play flow control apparatus comprises an optical mouse imaging assembly.

DESCRIPTION OF EMBODIMENTS OF THE INVENTION

Figure 1A:
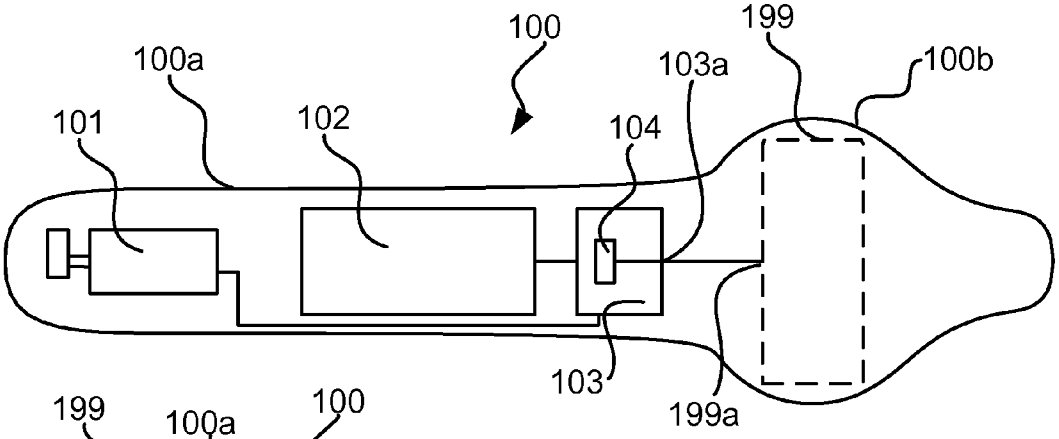
FIG. 1*a* illustrates a top view and FIG. 1*b* illustrates an end view of a sensual consumer product (SCP) in accordance with the preferred embodiment of the invention.
Figure 1B:
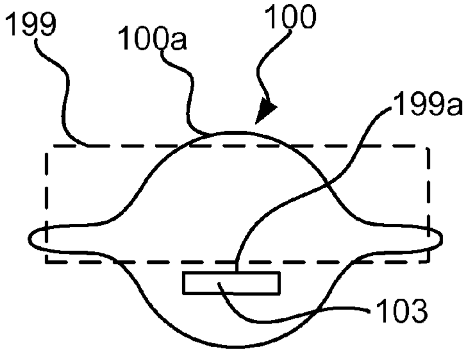

FIG. 1*a* illustrates a top view and FIG. 1*b* illustrates an end view of a sensual consumer product (SCP) 100 in accordance with the preferred embodiment of the invention. The SCP 100 is formed from a housing 100*a*, where the housing 100*a* comprises at least a deformable portion in the form of a first deformable portion 100*b*. Disposed within the housing 100*a* is an electric motor 101 and a battery compartment 102 for receiving of batteries, such as AAA batteries or rechargeable batteries. A play flow control apparatus 199 is disposed for receiving a user input and comprises an output port 199*a* for providing a play flow control signal. A control circuit 103 comprising a processor 104 is preferably embedded within the housing 100*a* and is coupled with the electric motor 101 and battery compartment 102 and comprises an input port 103*a* coupled with the output port 199*a* of the play flow control apparatus 199 for receiving of the play flow control signal therefrom.

Preferably an off centric weight is attached to a motor shaft as part of the electric motor 101 for causing vibrations to be produced by the motor 101 when in use. The play flow control apparatus 199 preferably other than comprises a mechanical switch that is coupled to the output port 199*a* such that the mechanical switch (not shown) is not utilized for affecting the play flow control signal.

Preferably the battery compartment is for accepting of a rechargeable battery, such as a lithium ion battery. Of course the use of alkaline batteries is also envisaged.

In use of the SCP 100, when the battery compartment 102 is provided with electrical power from batteries (not shown), a user input provided to the play flow control apparatus 199 is used to vary the play flow control signal for at least one of varying at least a mode of operation of the control circuit 103 and a rotational speed of the electric motor 101.

The user input that is provide to the play flow control apparatus 199 for varying of the play flow control signal is at least one of a frictional contact with the play flow control apparatus and a contact that causes deformation of the play flow control apparatus. Preferably contact with the SCP 100 from a small distance, such as a few millimeters, is also envisaged.

For example, the user input is at least one a deformation of the housing 100*a* resulting from a body part of the user interacting with the housing and causing deformation thereto and a frictional engagement of a body part of the user with the play flow control apparatus 199.

Since the body part of the user has a capacitance, a frictional engagement of the play flow control apparatus 199 with the body part of the user will result in a change of the play flow control signal in response to the capacitance of the user. In order to deform the housing, a bending of a portion of the housing or squeezing of a portion of the housing will result in a change in of the play flow control signal.

Figure 2A:
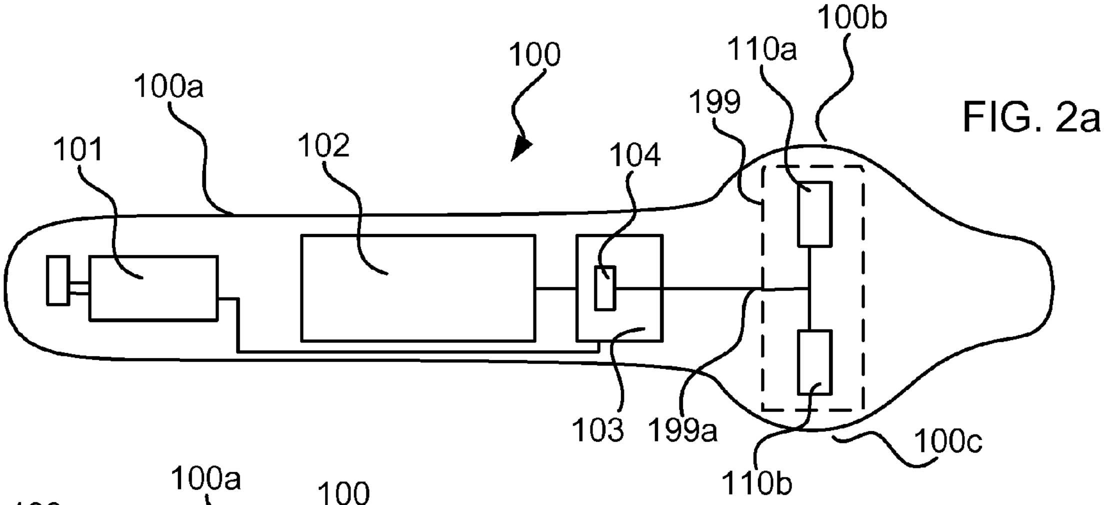
FIG. 2*a* illustrates the SCP from a top view, where the play flow control apparatus comprises at least a transducer.
Figure 2B:
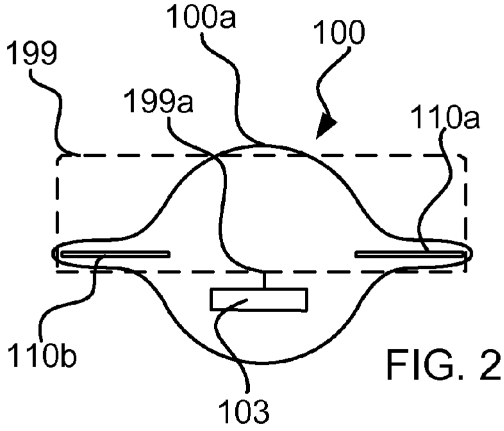
FIG. 2*b* illustrates the play flow control apparatus in an other than deformed state, or a relaxed state
Figure 2C:
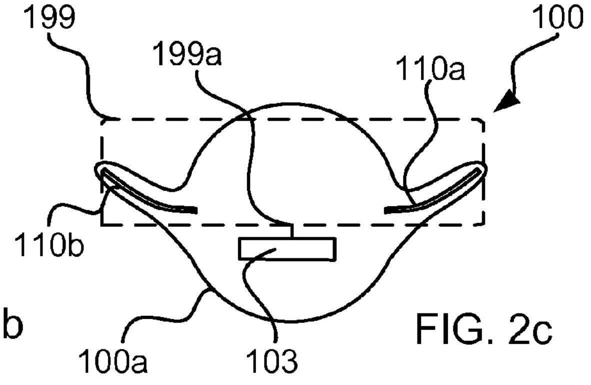
FIG. 2*c* illustrates the play flow control apparatus in the deformed state.

Referring to FIG. 2*a*, the SCP 100 is illustrated from a top view and the play flow control apparatus 199 comprises at least a transducer 110*a* and 110*b* coupled with the processor 104 through the output port 199*a* and disposed within the at least a deformable portion 100*b*. As is shown in FIGS. 2*b* and 2*c*, where FIG. 2*b* illustrates the play flow control apparatus 199 in an other than deformed state, otherwise known as a relaxed state, and where in FIG. 2*c* the play flow control apparatus 199 in the deformed state, deforming of the at least a deformable portion 100*b* causes deformation to the at least a transducer, 110*a* and 110*b*, which changes the play flow control signal. Preferably the at least a transducer 110*a* and 110*b* is one of an electromechanical type and an electroacoustic type and an electroactive polymer type and a strain gauge. For example, if the at least a transducer 110*a* and 110*b* is in the form of a bend sensor that upon being deformed through bending changes its electrical resistance properties, then the change in the electrical resistance properties varies the play flow control signal.

FIG. 3*a* illustrates a top view and FIG. 3*b* illustrates an end view of a sensual consumer product (SCP) 100 when the play flow control apparatus comprises a capacitance sensor assembly 111 for sensing an external capacitance, such as that of a body part of the user. In addition, the capacitance sensing assembly 111 comprises a capacitance sensing printed circuit board (PCB) 111*a* and a capacitance sensing circuit 111*b* coupled with the output port 199*a* for providing a capacitance electrical signal for varying of the play flow control signal. In addition, the capacitive sensing PCB 111*a* includes a first end 111*aa* and a second end 111*ab* disposed opposite each other.

In use of the SCP 100, when a body part of the user interacts with the capacitance sensor 111, the capacitance sensor provides a capacitance electrical signal to vary the play flow control signal. Varying of the external capacitance as provided to the capacitance sensing PCB assembly 111 varies the capacitance electrical signal in response to external capacitance variation as detected by the capacitance sensing circuit 111*b*.

For example if the user places a body part such as their finger towards the first end 111*aa* of the capacitance sensing PCB 111 the RPM of the motor 101 is at a first RPM and when the user places their finger towards the second end 111*ab* of the capacitance sensing PCB 111*a* the RPM of the motor 101 is at a second RPM. Preferably as the user slides their finger between the first end 111*aa* of the capacitance sensing PCB 111 and the second end 111*ab* of the capacitance sensing PCB through frictional contact with the play flow control apparatus 199, the RPM of the motor 101 varies approximately linearly between the first and second RPMs.

FIG. 4*a* illustrates a top view and FIG. 4*b* illustrates an end view of a sensual consumer product (SCP) 100 when the play flow control apparatus comprises an optical mouse imaging assembly 401, which is well known to those of skill in the art, comprising an imaging sensor 401*a* and an optical path 402, where the optical mouse imaging assembly 401 is for providing a movement signal for affecting the play flow control signal in response a movement detected within the within the optical path 402 of the optical mouse imaging assembly 401. Preferably a transparent window 402*a* disposed in the optical path 402 of the optical mouse imaging assembly w401, where this transparent window 402*a* and the housing are coupled together to allow for providing waterproofing to the coupling therebetween.

Preferably the optical mouse imaging assembly is for sensing movement of an object past this assembly 111 in at least two approximately orthogonal directions. Upon a user moving their finger across the transparent part 111*a*, output signals are provided from the optical mouse imaging assembly 111, and the play flow control signal is varied, where this control signal results in at least one of varying of the motor 101 RPM and a mode of operation of the control circuit 103. For example, if the user moves their finger past the optical mouse imaging assembly 111 in a horizontal direction the mode of operation of the control circuit 103 is varied and upon the user moving their finger past the optical mouse imaging assembly 111 in a vertical direction, the RPM of the motor 101 is varied in accordance with program instructions stored within the processor 104.

In another example, as the user moves their finger in a first horizontal direction past the optical mouse imaging assembly 111, the RPM of the motor increases and as the user moves their finger in a second horizontal direction past the optical mouse imaging assembly 111 the RPM of the motor decreases.

The processor 104, comprising instructions stored therein, controls the motor 101 by providing a predetermined pulse width modulation (PWM) to input ports thereof. By varying the PWM applied to the motor 101 the RPM of the motor is varied. Varying of the playflow control signal results in the processor 104 interpreting these variations and to vary the rotational speed of the motor 101 and to vary a mode of operation of the control circuit 103. For example, the mode of operation of the control circuit 103 is one of: enabling rotation of the motor 101, disabling rotation of the motor 101 and transitioning between enabling rotation of the motor 101 and disabling rotation of the motor 101.

Referring to FIG. 2*c*, when the at least a deformable portion 100*b* and 100*c* is deformed through bending, the RPM of the motor is increased and as the at least a deformable portion 100*b* and 100*c* is other than deformed FIG. 2*b* the RPM of the motor is decreased. As such, in such a mode of operation, the RPM of the motor is approximately proportionate to the deformation of the at least a deformable portion 100*b* and 100*c*.

In the case when the at least a transducer 110*a* and 110*b* is in the form of a bend sensor, as the bend sensor is deformed, such as a flexible sensor from Flexpoint™, its resistance changes. The change in resistance is provided to the processor 104, where instructions in execution with the processor determine a PWM to be provided to the motor input ports in dependence upon the resistance change.

Preferably the sensor disclosed within the embodiments of the invention is able to be used in a wet environment without adverse effects. Further preferably, as the user mechanically interacts with the As such, as the user interacts with the SCP 100, the motor 101 RPM will vary in proportion to an intensity of the interaction. For example, the harder the 199 is squeezed, the faster the motor 101 RPM. Preferably the motor RPM varies with the pressure applied to the 199, such that for less pressure the motor RPM is slower and for more pressure the motor RPM is higher.

Figure 5:
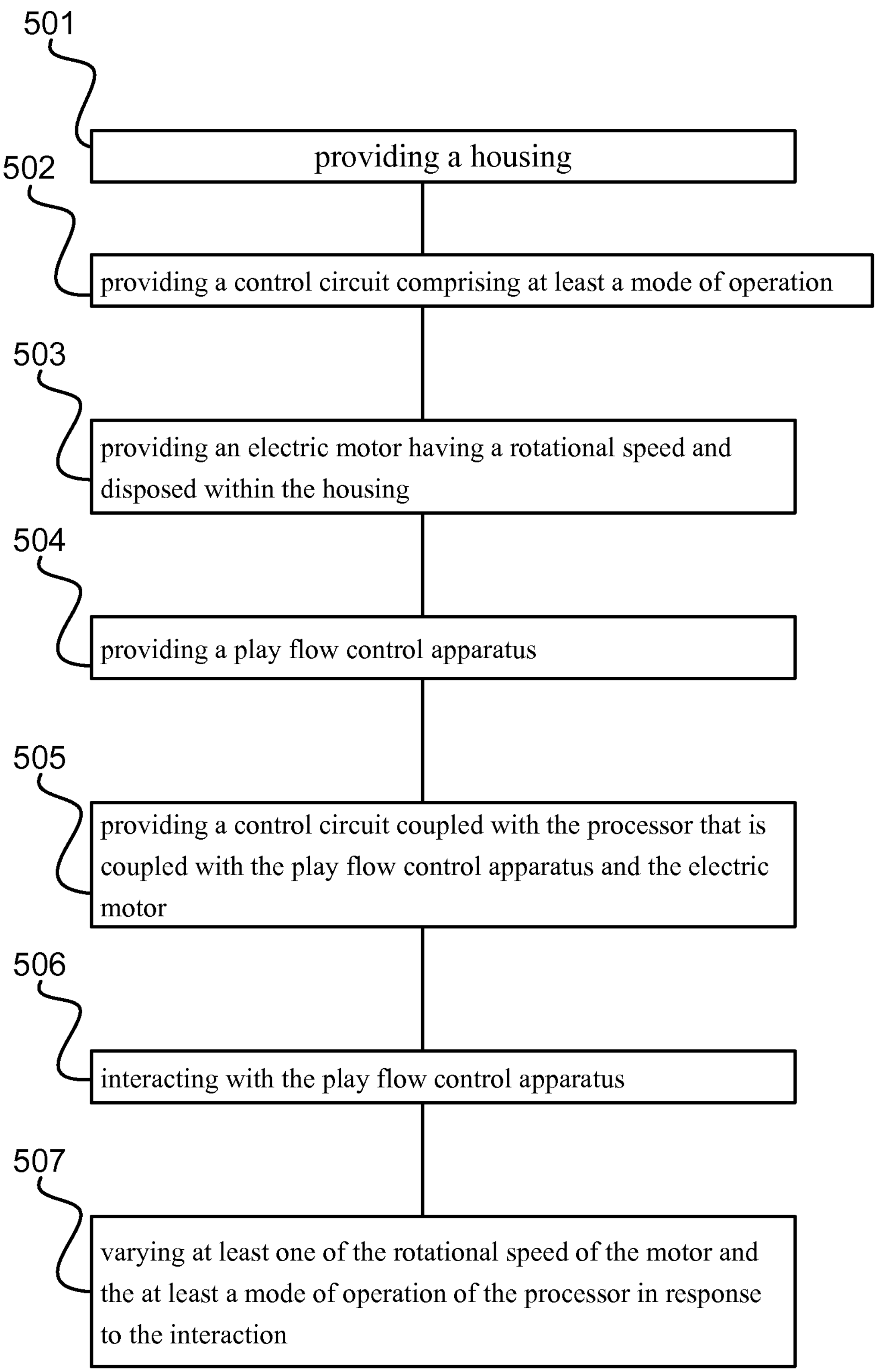
FIG. 5 illustrates a method of operation of the SCP in accordance with the embodiment of the invention.

FIG. 5 illustrates a method of operation of the SCP 100 in accordance with the embodiment of the invention, wherein firstly a housing 100*a* is provided in step 501. A processor 104 comprising at least a mode of operation is provided in step 502. An electric motor 101 having a rotational speed is provided in step 503. A play flow control apparatus is provided in step 504, where it is coupled with a control circuit coupled with the processor that is coupled with the play flow control apparatus and the electric motor, in step 505. Interacting with the play flow control apparatus is provided in step 506 and varying at least one of the rotational speed of the motor and the at least a mode of operation of the control circuit in response to the interaction is provided in step 507.

Advantageously, enabling a mode of operation of control circuit is performed by the user through interacting with the play flow control apparatus by either touching it for a predetermined period of time in a predetermined location along the play flow control apparatus, or by squeezing of the play flow control apparatus by squeezing or bending it for a predetermined period of time in a predetermined location along the play flow control apparatus. This would be an example of a waking up mode of operation for the control circuit 103. A shutting down mode of operation of the control circuit 103 is envisaged by using a similar approach. There is a plurality of options for how to interact with the play flow control apparatus. For varying the mode of operation and of the motor RPM.

Advantageously, the embodiment of the invention provides a more natural method of interaction with the SCP 100 that preferably does not utilize pushing of buttons for mechanical switching and relies more on squeezing and touching. Through the combination of the various sensors that are used within the play flow control apparatus, complex interaction behaviors with the SCP 100 are envisaged for controlling the play flow thereof for resulting in improved sensual experience with the SCP. Through the use of more natural motions, such as those of squeezing and touching, which are more analog in nature and not as digital as a mechanical switch, fluid motor RPMs are envisaged that are approximately proportional to intensities of interaction with the play flow control apparatus, where interacting with the play flow control apparatus varies at least one of the rotational speed of the motor and the at least a mode of operation of the control circuit in proportion to an intensity of the interaction.

Numerous other embodiments may be envisaged without departing from the spirit or scope of the invention.

What I claim is:

1. A sensual consumer product comprising:

an electric motor having a rotational speed;

a battery compartment;

a housing having disposed therein the electric motor and the battery compartment, wherein the housing comprises at least a deformable portion;

a play flow control apparatus disposed for receiving a user input and comprising an output port for providing a play flow control signal;

a control circuit comprising a processor coupled with the electric motor and battery compartment and comprising an input port coupled with the output port of the play flow control apparatus for receiving the play flow control signal therefrom;

at least a transducer coupled with the processor through the output port and disposed within the at least a deformable portion, wherein deforming of the at least a housing deformable portion deforms the at least a transducer which changes the play flow control signal in response to the deformation thereof;

the processor for interpreting variations in the play flow control signal and varying the rotational speed of the electric motor proportionally to the interpreted variations in the play flow control signal.

2. A sensual consumer product according to claim 1, wherein the transducer is one of an electromechanical type, an electroacoustic type, an electroactive polymer type, and a strain gauge.

3. A sensual consumer product according to claim 1, wherein the transducer is a bend sensor that upon being deformed through bending changes its electrical resistance properties where a change in the electrical resistance properties varies the play flow control signal.

4. A sensual consumer product according to claim 1 comprising no mechanical switches.

5. The sensual consumer product of claim 1 wherein the processor is provided for interpreting variations in the play flow control signal and varying the mode of operation of the control circuit.

6. A method comprising:

providing a housing;

providing a processor comprising instructions for being executed therein;

providing an electric motor having a rotational speed and disposed within the housing;

providing a play flow control apparatus including a deformable portion;

providing a control circuit having at least a mode of operation and comprising the processor, which is coupled with the play flow control apparatus and the electric motor;

providing a transducer coupled with the control circuit and disposed in proximity of the deformable portion;

deforming of the deformable portion and deforming the transducer;

interpreting variations in interactions with the play flow control apparatus;

changing the play flow control signal in response to the interpreting variations in interactions with the play flow control apparatus;

varying the rotational speed of the motor proportionally to the interpreting of variations in the interactions with the play flow control apparatus.

7. A method according to claim 6 wherein varying the rotational speed of the motor proportionally to the interpreting of variations in the interactions with the play flow control apparatus comprises varying the rotational speed of the motor in proportion to an intensity of the interaction.

8. The method of claim 6 further comprising varying a mode of operation of the control circuit in response to the interpreting of variations in the interactions with the play flow control apparatus.

9. A sensual consumer product according to claim 6, wherein the transducer is a bend sensor that upon being deformed through bending changes its electrical resistance properties where a change in the electrical resistance properties varies the play flow control signal.

10. A sensual consumer product comprising:

an electric motor having a rotational speed;

a battery compartment;

a housing having disposed therein the electric motor and the battery compartment, wherein the housing comprises a deformable portion;

a play flow control apparatus comprising at least one of: a transducer, an optical mouse imaging assembly, and a capacitance sensing assembly, the play flow control apparatus disposed for receiving a user input and comprising an output port for providing a play flow control signal;

a control circuit comprising at least a mode of operation and comprising a processor, where the control circuit is coupled with the electric motor and the battery compartment and comprising an input port coupled with the output port of the play flow control apparatus for receiving the play flow control signal therefrom;

at least a transducer coupled with the processor through the output port and disposed within the deformable portion, wherein deforming of the deformable portion deforms the at least a transducer which changes the play flow control signal in response to the deformation thereof;

the processor for interpreting variations in the play flow control signal and varying the rotational speed of the electric motor proportionally to the interpreted variations in the play flow control signal; and the processor for interpreting variations in the play flow control signal and varying the mode of operation of the control circuit.

11. A sensual consumer product according to claim 10 comprising no mechanical switches.

12. A sensual consumer product according to claim 10, wherein the transducer is a bend sensor that upon being deformed through bending changes its electrical resistance properties where a change in the electrical resistance properties varies the play flow control signal.

* * * * *